United States Patent [19]

Merrill

[11] 4,347,935

[45] Sep. 7, 1982

[54] METHOD AND APPARATUS FOR ELECTROSTATICALLY SORTING BIOLOGICAL CELLS

[75] Inventor: John T. Merrill, Berkeley, Calif.

[73] Assignee: The United States of America as represented by the United States Department of Energy, Washington, D.C.

[21] Appl. No.: 39,527

[22] Filed: May 16, 1979

[51] Int. Cl.³ ............................................. B07C 5/342
[52] U.S. Cl. .................................... 209/3.2; 209/579; 209/588; 209/932; 250/222 PC; 324/71 CP; 356/72
[58] Field of Search .......................... 209/3, 4, 3.1, 3.2, 209/3.3, 576, 577, 588, 579, 932; 356/36, 72, 73; 250/222 PC; 324/71 CP

[56] References Cited

U.S. PATENT DOCUMENTS

| | | |
|---|---|---|
| 3,380,584 | 4/1968 | Fulwyler . |
| 3,656,171 | 4/1972 | Robertson . |
| 3,710,933 | 1/1973 | Fulwyler et al. . |
| 3,826,364 | 7/1974 | Bonner et al. ............... 209/3.1 |
| 3,836,912 | 9/1974 | Ghougasian et al. . |
| 3,910,702 | 10/1975 | Corll . |
| 3,963,606 | 6/1976 | Hogg ........................ 209/3 |
| 4,009,435 | 2/1977 | Hogg . |
| 4,148,718 | 4/1979 | Fulwyler ................... 209/3.1 |

OTHER PUBLICATIONS

Merrill et al.; "Investigations in High-Precision Sorting"; 9-16-78; Revision 1.
Merrill et al.; "Investigations in High-Precision Sorting"; 1979, Journal of Histochemistry and Cytochemistry.
Merrill et al.; "Investigations in High-Precision Sorting"; poster Display; 4/78.
Merrill et al.; "Investigations in High-Precision Sorting"; Dept. of Energy Tech. Rep. No. UCRL-80861, 3-7-78.
Herzenberg et al.; "Fluorescence-activated Cell Sorting"; *Scientific American*, Mar. 1976, pp. 108-117.

*Primary Examiner*—Joseph J. Rolla
*Attorney, Agent, or Firm*—Clifton E. Clouse, Jr.; Roger S. Gaither; James E. Denny

[57] ABSTRACT

An improved method of sorting biological cells in a conventional cell sorter apparatus includes generating a fluid jet containing cells to be sorted, measuring the distance between the centers of adjacent droplets in a zone thereof defined at the point where the fluid jet separates into descrete droplets, setting the distance between the center of a droplet in said separation zone and the position along said fluid jet at which the cell is optically sensed for specific characteristics to be an integral multiple of said center-to-center distance, and disabling a charger from electrically charging a specific droplet if a cell is detected by the optical sensor in a position wherein it will be in the neck area between droplets during droplet formation rather than within a predetermined distance from the droplet center.

5 Claims, 5 Drawing Figures

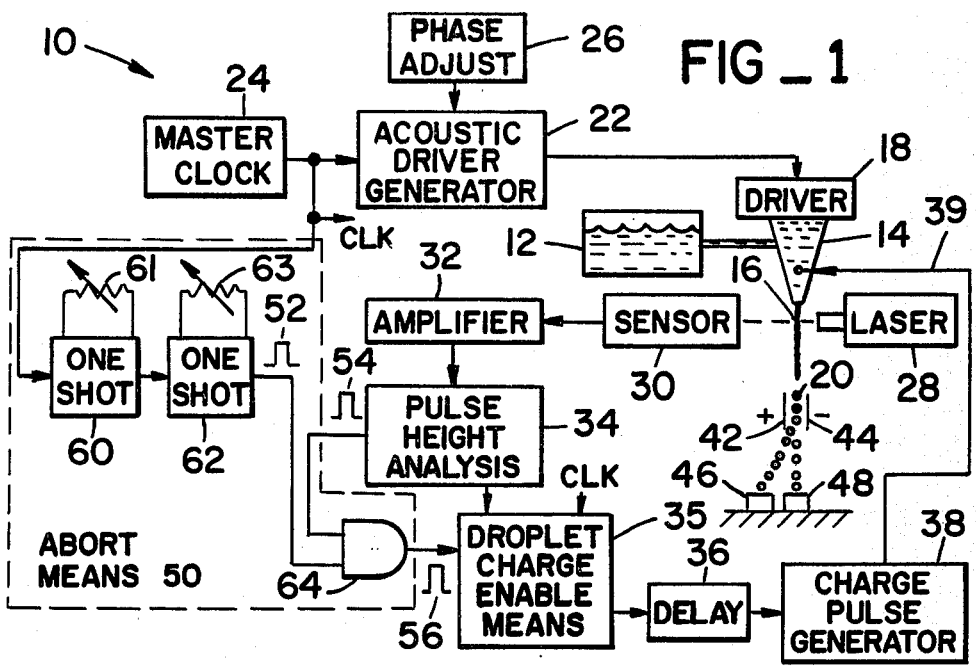
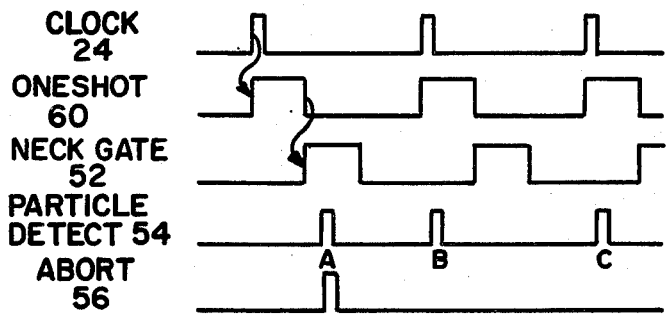
FIG_2
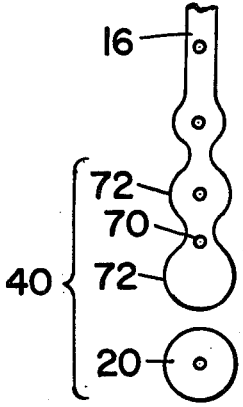
FIG_3A
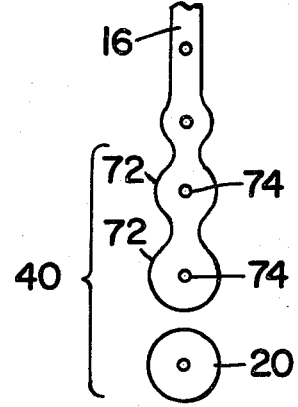
FIG_3B
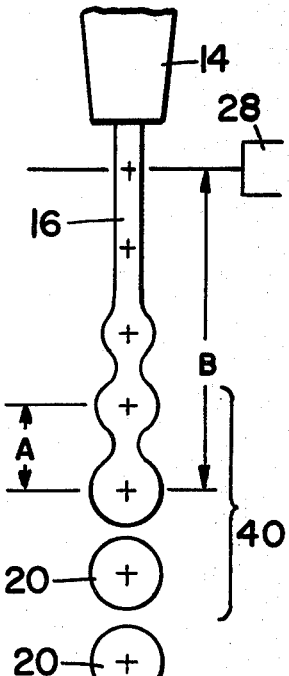
FIG_4

METHOD AND APPARATUS FOR ELECTROSTATICALLY SORTING BIOLOGICAL CELLS

BACKGROUND OF THE INVENTION

The invention described herein was made at Lawrence Livermore Laboratory in the course of, or under, Contract No. W-7405-ENG-48 between the U.S. Dept. of Energy (formerly Energy Research and Development Administration) and the University of California.

The present invention pertains to an apparatus for electrostatically sorting biological cells. More particularly, this invention relates to a method of more accurately sorting cells by detecting the presence of a cell in the neck area of a droplet during its formation and not selecting such droplets.

Devices for individually sorting biological cells by electrostatic means are well known in the art. One type of cell sorter apparatus generates a fluid jet of liquid containing cells suspended therein, and acoustically stimulates the fluid jet such that the jet breaks into a uniform stream of tiny droplets. Just below the nozzle, and before the droplets form, the jet is sensed for cells, e.g. by means of a laser light source and a photomultiplier detector, and the resulting electrical signals are used to charge the fluid exactly when the droplet containing a desired cell is being formed. The droplets then pass through an electrical deflection means which deflects each droplet according to its charge into an appropriate container. Those droplets which do not contain cells, or which contain cells that are not desired, remain uncharged and are not deflected. Sorting speeds of thousands of cells per second are obtainable with such devices.

The problem with such sorting systems is that the deflected stream of droplets tends to diverge instead of being narrow and well focused, making collection difficult, and in some cases impossible. This divergence is caused by the lack of uniformity in the size and charge of droplets. It is believed that this lack of uniformity is a result of the presence of a cell in the neck area between droplets during droplet formation. Since the cell must be either included in the lower droplet or in the adjacent upper droplet, some of the charged droplets will have a different mass. Further, since the conductivity of the cell is different from that of the carrying liquid, the charge imparted to the droplet will be different in magnitude if no cell is present therein. Thus, a method is needed for disabling the sorting of droplets having such different charges and masses, so that uniform deflection of desired droplets by the electrical deflection means is provided.

Therefore, it is an object of the present invention to provide an improved method and apparatus for electrostatically sorting biological cells, or other small particles suspended in a liquid, wherein the position of each particle is sensed prior to droplet formation, and only particles positioned within the body of a droplet rather than positioned in what will become a neck area between adjacent droplets, are selected for further sorting.

Another object of the present invention is to provide an improved method and apparatus for electrostatically sorting biological cells, which utilizes the advantages inherent in fluid jets vibraed at a proper frequency, to determine prior to droplet formation if a given sensed particle in said fluid jet is positioned for accurate sorting.

A further object of the present invention is to provide an improved method and apparatus for electrostatically sorting biological cells, which selects particles for sorting in a fluid jet by setting a timer to output an abort pulse equal to an abort interval, comparing this timed interval with a particle detect pulse, and aborting the sorting of a given particle if the detect pulse occurs while said abort pulse is on.

SUMMARY OF THE INVENTION

The present invention provides an improved method for electrostatically sorting biological cells, or other small particles suspended in a liquid, such that droplets of uniform size and charge are accurately deflected towards a small collection point. The present invention relies on the fact that a narrow fluid jet breaks up into a procession of droplets having remarkable uniformity and regularity if the nozzle or orifice that formed the jet is vibrated at a proper frequency.

Since the fluid jet is expelled from the sorter nozzle at a relatively rapid rate, the speed of the droplets remains constant at least in the distance traveled by the fluid between the nozzle and the droplet separation zone. Consequently, the distance between bulges in the fluid jet that will ultimately form into droplets remains constant along the fluid jet length. Thus, the present invention involves measuring the distance between adjacent droplets in the area of zone in which the droplets are formed from the fluid jet. Next, the position of the sensor means, i.e., where it crosses the path of the fluid jet above the droplet separation zone, is adjusted such that this position, with respect to the centerpoint of a droplet as it is being formed in the droplet separation zone, is an integral multiple of the distance between droplets. With the position of the sensor means known with respect to the point where a droplet is formed, timers are set to generate a pulse at a point in time indicating that a given cell detected by said sensor means will arrive in the neck between droplets in said zone. The improved method disables the charging means from charging this droplet, to prevent sorting thereof.

Other objects and advantageous features of the invention will be apparent in a description of a specific embodiment thereof, given by way of example only, to enable one skilled in the art to readily practice the invention which is described hereinafter with reference to the accompanying drawing.

BRIEF DESCRIPTION OF THE DRAWINGS

FIG. 1 is a partial schematic diagram of an electrostatic cell sorting system according to the present invention;

FIG. 2 is a timing diagram illustrating the operation of the circuit of FIG. 1;

FIG. 3A illustrates the fluid jet flow just as droplets are being formed, with a cell positioned in the neck between droplet bulges;

FIG. 3B illustrates the same fluid jet flow as in FIG. 3A but with a cell in a desired location within the droplet bulge; and FIG. 4 illustrates the distances along the length of the fluid jet to be measured in accordance with the present invention.

DESCRIPTION OF THE PREFERRED EMBODIMENT

Reference will now be made in detail to a present preferred embodiment of the invention, an example of which is illustrated in the accompanying drawing. While the invention will be described in connection with a preferred embodiment, it will be understood that it is not intended to limit the invention to that embodiment. On the contrary, it is intended to cover all alternatives, modifications, and equivalents as may be included within the spirit and scope of the invention as defined by the appended claims.

Referring now to the drawing, an electrostatic cell sorting system according to the present invention is shown in partial schematic diagram form at 10 in FIG. 1. A fluid solution containing small particles to be sorted is caused to flow from a storage container 12 through a nozzle 14. The fluid is forced through nozzle 14 under pressure to generate a narrow fluid jet 16 containing particles in single file. The nozzle 14 is continually vibrated axially by means of a driver 18, causing the fluid jet 16 to separate into a uniform flow of equally-spacedapart droplets, as seen at 20, with each droplet normally containing a single particle. (See also FIG. 3.) The nozzle driver 18 is pulsed by means of an acoustic driver generator 22 under the control of a master clock 24. The acoustic driver generator 22 includes a phase adjust 26, the functioning of which will be described hereinbelow.

To detect particles in the fluid jet 16, a sensor means is provided. Such means may include a laser light source 28 which illuminates the jet 16. The illuminated jet 16 is then detected by a sensor 30, such as a photomultiplier tube. Sensor 30 outputs an electric pulse whenever a particle in said fluid jet 16 passes this illumination point.

The sensor means may also include an amplifier 32 for amplifying the output of sensor 30 and a pulse-height-analysis system 34 or the like for analyzing said amplified pulse. The output of the pulse-height-analysis system 34 is input to a droplet charge enable means 35. If the particle sensed is of a type that is to be sorted, as determined by said system 34, said means 35 outputs a sort signal, a charge enable signal, coincident with said clock 24 signal. This sort signal is fed through a delay 36 to a charge pulse generator 38. The delay 36 acts on the charge pulse generator 38 to cause an electrode 39, or the like, to energize the fluid jet at the optimum point when the droplet containing the desired cell is forming, i.e. in a droplet separation zone 40, as seen in FIGS. 3 and 4. The delay 36 is timed for a delay equal to the time of passage of a particle from point of contact of said laser 28 on said fluid jet 16 and said droplet separation point. Thus, the decision as to whether or not to sort a specific particle is made at the time that the particle is detected by the sensor means 30. This sort decision is made possible since the formation of droplets is a synchronous process, with delay 36 providing the memory needed to remember the sort decision until the particle to be sorted is in the droplet separation zone and ready to be charged by the charge pulse generator 38.

For charging of a given droplet, note that the electrode 39 from the charge pulse generator 38 may contact the fluid within nozzle 14 since the fluid jet 16 provides a conducting path to the droplet separation zone 40. At the end of each sort signal, the fluid jet 16 is grounded so that subsequent droplets have a neutral charge until the jet is again energized by the generator 38.

Droplets that separate from the fluid jet 16 while it is charged by said charge pulse generator 38 retain their charge. These droplets then pass between two charged plates 42 and 44. Plates 42, 44 establish a constant electrostatic field across the path of the droplets. Charged droplets are deflected by plates 42 and 44, whereas uncharged droplets continue on their normal course. Deflected droplets fall into a container 46. Uncharged droplets fall into a container 48.

The present invention provides means for aborting the particle sorting process when a particle is detected in a position where it will fall in a neck area between droplets during droplet formation, rather than in a central location within a given droplet. An exemplary abort means is shown at 50 in FIG. 1. Abort means 50 includes means for generating a timing pulse, indicated as neck gate pulse 52, as a function of the clock pulses generated by master clock 24. Neck gate pulse 52 is timed to remain on for an abort interval which corresponds to the maximum period of occurrence of a particle positioned in said neck area between droplets. This pulse is then compared with a particle detect pulse 54, generated by said pulse height analysis system 34. An abort pulse 56 is generated if said particle detect pulse occurs while said neck gate pulse 52 is on. Abort pulse 56 is then coupled to the droplet-charge-enable means 35 for disabling the sorting of this droplet.

More specifically, the neck gate pulse is generated by two one-shots illustrated at 60 and 62. One-shot 60 is turned on by each master clock 24 pulse. As described in more detail below, the sorter apparatus is initially calibrated such that a clock pulse from clock 24 occurs at a point in time, less the delay created by delay 36, equal to when each droplet is just about to separate from the fluid jet 16 in the droplet separation zone 40. That is, each clock 24 pulse occurs at a time coincident with what will become the center point of each droplet as said droplet to be crosses the path of said sensor means.

Thus, the midpoint between adjacent clock 24 pulses corresponds to the neck area between adjacent droplets. One-shot 62 controls the duration of neck gate pulse 52, and thereby the abort interval. One-shot 60 when it times out and goes off, causes one-shot 62 to turn on. Consequently the on-time duration of one shot 60 controls the onset time of one-shot 62 and its neck gate pulse 52 output. One-shot 60 can therefore be adjusted to ensure that the abort interval is centered between adjacent clock 24 pulses.

Adjustment of the on time of both one-shot 60 and one-shot 62 is enabled with respective potentiometers 61 and 63. Potentiometers 61 and 63 thus enable the particle sorting process to be adjustable to provide a sort which may be more or less critical of particle position within a given droplet, depending on the length of time one-shot 62 remains on. Of course, one-shot 62 should be adjusted to time out and go off before the occurrence of the next clock 24 pulse.

The neck gate pulse 52 is AND'ed to the cell detect pulse 54 via a conventional AND gate 64 to generate the abort pulse 56. In other words, gate 64 functions to output an abort pulse 56 if a cell is detected at any time while one-shot 62 is on.

The abort pulse 56 is coupled into the droplet-charge-enable means 35 along with the clock 24 pulse, shown as CLK. The other input to charge enable means 35 is the output of the pulse height analysis means 34. Means 35 functions as an AND gate, such that an input to delay 36 for a given droplet from said means 35 is generated only when an abort pulse 56 is not present. That is, abort pulse 56 acts to disable the droplet charge enable means 35 whenever a particle is detected in a position where it will end up in said droplet neck area.

FIG. 2 illustrates the operation of the abort means according to one embodiment of the present invention. As seen in FIG. 2, the clock 24 pulse acts to turn on one-shot 60. Thereafter, when one-shot 60 goes off this causes one-shot 62 to go on thereby generating the neck gate pulse 52. The particle detect 54 curve illustrates a situation where a first pulse A corresponds to a particle detected at such a position that it will end up as a particle in the neck between droplets. As is seen, this causes the generation of an abort pulse 56, since pulse A occurs while the neck gate pulse 52 is on. Subsequent particles detected at B and C indicate a particle position near a droplet center wherein sorting is allowed to take place. Since the particles detected at B and C do not occur during the on time of the neck gate pulse 52, no abort pulse is generated for these particles.

FIG. 3A illustrates an exemplary fluid jet 16 flow just as droplets are being formed, with a particle, such as a cell 70, positioned in the neck between adjacent droplet bulges 72. Properly spaced particles centrally located in respective bulges 72 are shown at 74 (FIG. 3B). This illustrates the desired situation wherein adjacent droplet bulges 72 each have properly spaced particles 74 in respective central locations therein. The present invention acts to abort the sorting of the droplet 72 being formed as shown in FIG. 3A, due to the obvious possibility that it will not contain the particle 70.

To ensure that the timing pulse generated by one-shot 62, the neck gate pulse 52, is on for a time representative of when a particle would be in a neck area, some preliminary steps are performed. Initially, the charge pulse generator 38 needs to be in phase with the generation of droplets, such that a maximum charge is imparted to each droplet as it is formed. Therefore, with no particles in fluid jet 16, the phase of the clock 24 pulse is adjusted by the phase adjust 26 to modify the driver 18 signal to nozzle 14, such that the charge pulse generator charges the fluid jet 16 only when the fluid jet 16 is midway between droplet breakoffs. Since no particles are detected, the clock pulse is directly fed to delay 36 to thereby actuate the charge pulse generator 38 for each droplet. Correct phasing can be seen when the fluid jet 16 is sharply deflected either to the left or to the right, thereby indicating no partially charged droplets.

So that the center of what will become a droplet in the droplet separation zone passes across the point on the fluid jet 16 illuminated by said laser 28 coincident with the occurrence of a clock pulse, the following needs to be performed. Coincidence is needed so that the clock pulse as delayed by delay 36 acts to turn on or off said charge pulse generator 38 when that specific droplet is being formed in the droplet separation zone 40.

Thus, the present invention requires the measurement of the distance between the centers of adjacent droplets in said droplet separation zone 40. This measurement is illustrated in FIG. 4 at A. To make this measurement in a constantly moving fluid jet stream, the clock 24 pulse is also input to a stroboscopic light to thereby freeze the movement of the droplets in the droplet separation zone 40.

With the distance between the centers of adjacent droplets known, the point at which the laser light source 28 illuminates the fluid jet 16 must be adjusted to be a distance equal to an integral multiple of the above described distance between droplet centers. This distance is illustrated in FIG. 4 at B.

Consequently, the occurrence of a clock pulse will be coincident with the detection of a particle, if the particle is centrally located within a given droplet. This is accurate since the distance between forming droplets in the fluid jet 16 remains essentially constant at least along the path of said jet between the output of nozzle 14 and the droplet separation zone 40. Note that the measurement of the distance between adjacent droplet centers must be repeated for each use of the sorter apparatus, due to the variation in this distance as a result of changes in air humidity, air pressure, etc.

It is to be understood that the foregoing description is merely illustrative of a preferred embodiment of the invention and that the scope of the invention is not to be limited thereto but is to be determined by the scope of the appended claims.

What is claimed is:

1. A method for sorting small particles using apparatus which includes means for generating a fluid jet having said particles suspended therein, sensor means across the path of said fluid jet for generating a particle detect pulse and a droplet-charge-enable signal in response to a selected characteristic of a particle, means for acoustically pulsing said fluid jet to cause separation thereof into droplets in a discrete separation zone, said pulsing means including a clock generating means for generating a clock pulse for each droplet to be formed, electrical charging means operatively coupled to said fluid jet, electrical delay means having a period of delay equal to the time of passage of a particle passing from the sensor means to said droplet separation zone, whereby each particle-containing droplet, as it forms, is impressed with a charge by said charging means of a magnitude controlled by said droplet-charge-enable signal generated for that droplet, electrical deflection means positioned with respect to said droplet path, said electrical deflection means deflecting a droplet according to its charge, the method comprising the steps of:
   (a) generating a timing pulse as a function of said clock pulse, wherein said timing pulse remains on for an abort interval corresponding to when said sensor means would detect a particle in a position where it will fall between adjacent droplets during droplet formation;
   (b) comparing said abort interval pulse with said particle detect pulse and outputting an abort pulse if said detect pulse is detected during said abort interval; and
   (c) disabling said charge enable signal in response to the generation of said abort pulse.

2. A method for sorting small particles using apparatus which includes means for generating a fluid jet having said particles suspended therein, sensor means across the path of said fluid jet for generating a particle detect pulse and a droplet-charge-enable signal in response to a selected characteristic of a particle, means for acoustically pulsing said fluid jet to cause separation thereof into droplets in a discrete separation zone, said pulsing means including a clock generating means for generating a clock pulse for each droplet to be formed, electrical charging means operatively coupled to said fluid jet, electrical delay means having a period of delay equal to the time of passage of a particle passing from the sensor means to said droplet separation zone, whereby each particle-containing droplet, as it forms, is impressed with a charge by said charging means of a magnitude controlled by said droplet-charge-enable signal generated for that droplet, electrical deflection means positioned with respect to said droplet path, said electrical deflection means deflecting a droplet according to its charge, the method comprising the steps of:

(a) determining the distance between the centers of adjacent droplets in said droplet separation zone;

(b) setting the distance between the center of a droplet in the droplet separation zone as synchronized by said clock pulse and the point at which said sensor means crosses said fluid jet path to be an integral multiple of said distance between droplet centers;

(c) actuating a first timer upon the occurrence of said clock pulse;

(d) setting said first timer to time out some time prior to the occurrence of the next clock pulse;

(e) actuating a second timer upon the occurrence of the time out of said first timer;

(f) setting said second timer to time out at the end of a predetermined abort interval; and (g) disabling said charge enable signal if a particle detect pulse occurs while said second timer is in its actuated state.

3. The method of claim 2 wherein step (g) includes the steps of:

(i) comparing said particle detect pulse with said second timer and outputting an abort pulse if said detect pulse occurs while said second timer is in its actuated state; and (ii) disabling a charge-enable gate when an abort pulse occurs, said charge-enable gate acting in response thereto to prevent the coupling of said charge-enable signal to said electrical charging means.

4. In an apparatus for sorting small particles, including means for generating a fluid jet having said particles suspended therein, sensor means across the path of said fluid jet for generating a particle detect pulse and a droplet-charge-enable signal in response to a selected characteristic of a particle, means for acoustically pulsing said fluid jet to cause separation thereof into droplets in a discrete separation zone, said pulsing means including a clock generating means for generating a clock pulse for each droplet to be formed, electrical charging means operatively coupled to said fluid jet, electrical delay means having a period of delay equal to the time of passage of a particle passing from the sensor means to said droplet separation zone whereby each particle-containing droplet, as it forms, is impressed with a charge by said charging means of a magnitude controlled by said droplet charge enable signal generated for that droplet, electrical deflection means positioned with respect to said droplet path, said electrical deflection means deflecting a droplet according to its charge, an improved apparatus for aborting the sorting of a selected droplet when a particle in such droplet is detected in a position wherein it will fall in the neck area thereof during droplet formation, said apparatus comprising:

timer means for generating a timing pulse as a function of said clock pulse, wherein said timing pulse is defined to remain on for an abort interval corresponding to when said sensor means would detect a particle in a position where it will fall in the neck area of a droplet during droplet formation;

means for comparing said timing pulse with said particle detect pulse and generating an abort pulse if said detect pulse is generated during said abort interval; and means for disabling said charge enable signal in response to the generation of said abort pulse.

5. In an apparatus for sorting small particles, including means for generating a fluid jet having said particles suspended therein, sensor means across the path of said fluid jet for generating a particle detect pulse and a droplet-charge-enable signal in response to a selected characteristic of a particle, means for acoustically pulsing said fluid jet to cause separation thereof into droplets in a discrete separation zone, said means including a clock generating means for generating a clock pulse for each droplet to be formed, electrical charging means operatively cooled to said fluid jet, electrical delay means having a period of delay equal to the time of passage of a particle passing from the sensor means to said droplet separation zone whereby each particle-containing droplet, as it forms, is impressed with a charge by said charging means of a magnitude controlled by said droplet charge enable signal generated for that droplet, electrical deflection means positioned with respect to said droplet path, said electrical deflection means deflecting a droplet according to its charge, an improved apparatus for aborting the sorting of a selected droplet when a particle in such droplet is detected in a position wherein it will fall in the neck area thereof during droplet formation, said apparatus comprising:

timer means for generating a timer pulse as a function of said clock pulse, wherein said timing pulse is defined to remain on for an abort interval corresponding to when said sensor means would detect a particle in a position where it will fall in the neck area of a droplet during droplet formation;

said timer means comprising first and second one-shots, said clock pulse operatively connected to said first one-shot such that said first one-shot goes on at the occurrence of each clock pulse, said first one-shot operatively connected to said second one-shot such that said second one-shot goes on when said first one-shot times out and goes off, said second one-shot remaining on for a predetermined abort interval;

means for comparing said timing pulse with said particle detect pulse and generating an abort pulse if said detect pulse is generated during said abort interval; and means for disabling said charge enable signal in response to the generation of said abort pulse.

* * * * *